(12) United States Patent
Ling et al.

(10) Patent No.: US 9,999,445 B2
(45) Date of Patent: Jun. 19, 2018

(54) FULL-VAGINA SLEEVE CYLINDRICAL EXPANSION AND PNEUMOPERITONEUM INTEGRATED DEVICE

(71) Applicants: Andong Ling, Anhui (CN); Bin Ling, Anhui (CN)

(72) Inventors: Andong Ling, Anhui (CN); Bin Ling, Anhui (CN)

(*) Notice: Subject to any disclaimer, the term of this patent is extended or adjusted under 35 U.S.C. 154(b) by 184 days.

(21) Appl. No.: 14/912,162

(22) PCT Filed: Jul. 4, 2014

(86) PCT No.: PCT/CN2014/000645
§ 371 (c)(1),
(2) Date: Feb. 15, 2016

(87) PCT Pub. No.: WO2015/021735
PCT Pub. Date: Feb. 19, 2015

(65) Prior Publication Data
US 2016/0199094 A1    Jul. 14, 2016

(30) Foreign Application Priority Data

Aug. 16, 2013  (CN) .......................... 2013 1 0360259

(51) Int. Cl.
| A61B 17/42 | (2006.01) |
|---|---|
| A61B 17/00 | (2006.01) |
| A61B 17/02 | (2006.01) |
| A61B 17/34 | (2006.01) |
| A61B 1/303 | (2006.01) |

(52) U.S. Cl.
CPC .............. *A61B 17/42* (2013.01); *A61B 1/303* (2013.01); *A61B 17/00234* (2013.01); *A61B 17/0293* (2013.01); *A61B 17/3423* (2013.01); *A61B 17/3498* (2013.01); *A61B 17/4241* (2013.01); *A61B 2017/0225* (2013.01); *A61B 2017/345* (2013.01); *A61B 2017/348* (2013.01); *A61B 2017/3419* (2013.01);
(Continued)

(58) Field of Classification Search
CPC ...... A61B 17/42; A61B 1/303; A61B 17/0293
See application file for complete search history.

(56) References Cited

U.S. PATENT DOCUMENTS

| 5,514,133 A * | 5/1996 | Golub ................ A61B 17/3423 604/175 |
| 6,162,196 A * | 12/2000 | Hart ................... A61B 17/3462 604/167.02 |

FOREIGN PATENT DOCUMENTS

| CN | 101491463 A | 7/2009 |
| CN | 201365909 Y | 12/2009 |
(Continued)

*Primary Examiner* — Christian Sevilla

(57) ABSTRACT

A full-vagina sleeve cylindrical expansion and pneumoperitoneum integrated device, includes: an elastic embedded ring (1) and a sleeve (2). The elastic embedded ring (1) is made of elastic material and embedded inside a pelvic outlet. The elastic embedded ring (1) is capable of expanding in a natural state inside a vagina to tightly adhere to wall of the vagina, or being inflated into an annular ring which tightly adheres to the vagina wall so as to elastically expand a vagina tissue. The sleeve (2) is made of elastic material or a non-elastic material and is cylinder-shaped. A front end ring of the sleeve (2) is connected with the elastic embedded ring (1), and a rear end ring extends out of the vagina. An operation mask (3) is fixedly provided on the rear end ring.

2 Claims, 1 Drawing Sheet

(52) U.S. Cl.
CPC ......... *A61B 2017/3429* (2013.01); *A61B 2017/3466* (2013.01); *A61B 2017/3486* (2013.01)

(56) References Cited

FOREIGN PATENT DOCUMENTS

| | | |
|---|---|---|
| CN | 101617932 A | 1/2010 |
| CN | 101999912 A | 4/2011 |
| CN | 202179581 U | 4/2012 |
| CN | 103405251 A | 11/2013 |
| CN | 203400171 U | 1/2014 |
| EP | 2572664 A1 | 3/2013 |

* cited by examiner

FULL-VAGINA SLEEVE CYLINDRICAL EXPANSION AND PNEUMOPERITONEUM INTEGRATED DEVICE

CROSS REFERENCE OF RELATED APPLICATION

This is a U.S. National Stage under 35 U.S.C 371 of the International Application PCT/CN2014/000645, filed Jul. 4, 2014, which claims priority under 35 U.S.C. 119(a-d) to CN 201310360259.2, filed Aug. 16, 2013.

BACKGROUND OF THE PRESENT INVENTION

Field of Invention

The present invention relates to the field of an auxiliary surgical instrument, and more particularly to an auxiliary device utilized in the gynecologic minimally invasive surgery.

Description of Related Arts

The conventional gynecological laparoscopic operation technique utilizes a pneumoperitoneum method to fully expose the surgical field. The pneumoperitoneum method has advantages including a clear image, a small trauma on dominal wall of patient and a quick recovery, and thus is widely applied in gynecological operation. However, the method might involve a plurality of small incisions on the dominal wall, and thus scars are left.

The conventional vaginal operation adopts a natural channel which is more in accordance with physiological characteristics of the human beings, so as to avoid dominal wall traumas and achieve a more minimal invasion, and thus is widely applied in gynecological operation. However, per vagina operations are not capable of fully exposing the surgical field, and it is difficult to operate in narrow space.

SUMMARY OF THE PRESENT INVENTION

Accordingly, in order to avoid the disadvantages in the conventional art mentioned above, the present invention provides a full-vagina sleeve cylindrical expansion and pneumoperitoneum integrated device. As an auxiliary surgical instrument, the full-vagina sleeve cylindrical expansion and pneumoperitoneum integrated device combines advantages of the conventional gynecologic laparoscopic operations and the conventional vagina operations, enhances advantages and avoids disadvantages of the two kinds of operations, so as to achieve a more minimal invasion.

In order to solve the technical problems mentioned above, the present invention adopts technical solutions as follows.

A full-vagina sleeve cylindrical expansion and pneumoperitoneum integrated device, is characterized in comprising:

an elastic embedded ring which is made of elastic material and embedded inside a pelvic outlet, wherein the elastic embedded ring capable of expanding in a natural state inside a vagina to tightly adhere to a wall of the vagina, or being inflated into an annular ring which tightly adheres to the vagina wall so as to elastically expand a vagina tissue; and a sleeve which is made of elastic material or a non-elastic material and is cylinder-shaped;

wherein a front end ring of the sleeve is connected with the elastic embedded ring, and a rear end ring extends out of the vagina, an operation mask is fixedly provided on the rear end ring, an operation hole and an observation hole which are capable of being sealed are respectively provided on the operation mask, the operation mask serves as an end surface sealing plate, in such a manner that an inflatable sealed space is formed inside the vagina and the sleeve.

The characteristic of the full-vagina sleeve cylindrical expansion and pneumoperitoneum integrated device also lies in that a fixing supporter which is a liftable is provided thereon, and the operation mask is supported by the fixing supporter.

Compared with the conventional arts, beneficial effects of the present invention lie in following aspects.

1. The full-vagina sleeve cylindrical expansion and pneumoperitoneum integrated device of the present invention is used for achieving per vagina laparoscope.

Taking advantages of a natural orifice of a female, the device of the present invention is provided in a laparoscope for observation via the vagina. The device of the present invention has advantages of a clear surgical field and a noninvasive dominal wall. As the vagina is in a naturally closed state and the channel of the vagina is narrow, the device of the present invention is utilized for fully expanding the channel of the vagina, so as to ensure an abundant space for surgical instruments to pass in and out and operate and for forming pneumoperitoneum.

2. The full-vagina sleeve cylindrical expansion and pneumoperitoneum integrated device of the present invention takes advantages of pressure generated by formation of pneumoperitoneum in a laparoscopic operation to expand the sleeve. After a sleeve in a loose state is expanded by inflation, the sleeve extrudes an elastic vagina wall to expand towards a pelvic cavity which is roomy, so as to ensure that pressure in an abdominopelvic cavity and the vagina is steady and capable of communicating with each other during the process of gynecological vaginal laparoscopic operation, and that the a the vagina is spacious in the whole channel.

3. The operation mask of the device of the present invention is provided outside the vagina and supported by a fixing supporter, so as to ensure that the mask is in a stabilization state, i.e., the mask is firm installed for serving as a surgical instrument operation pivot, so as to ensure the precision of the operation. When the operation mask increases, distance among a plurality of operation holes increases, in such a manner that crossing collision of the surgical instruments is avoided. Furthermore, a diameter of the operation hole can be enlarged, so as to facilitate resection of large tissue specimens for taking out.

Reference numbers: 1-elastic embedded ring; 2-sleeve; 3-operation mask; 4-fixing supporter; 5-observation hole; 6-operation hole; 7-uterus; 8-vagina cavity; 9-inflation tube; 10-laparoscope; 11-handling tongs.

DETAILED DESCRIPTION OF THE PREFERRED EMBODIMENT

Figure 1:
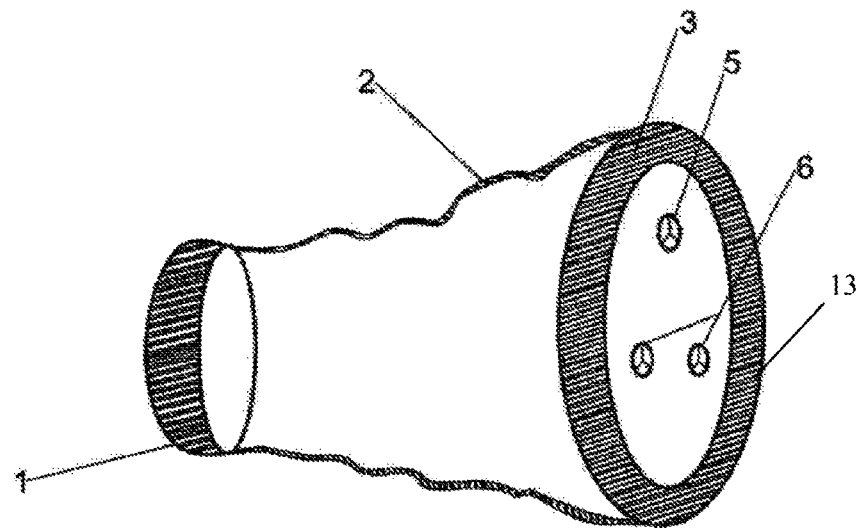
FIG. 1 is a structural schematic view of the full-vagina sleeve cylindrical expansion and pneumoperitoneum integrated device of the present invention.
Figure 2:
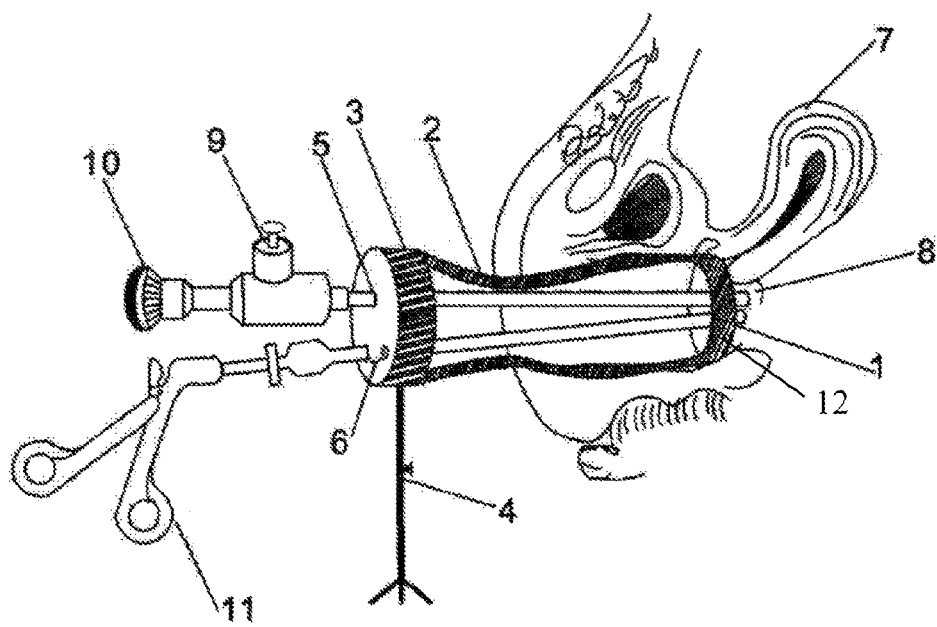
FIG. 2 is a schematic view of the full-vagina sleeve cylindrical expansion and pneumoperitoneum integrated device of the present invention in a service mode.

Referring to FIG. 1 and FIG. 2 of the drawings, according to a preferred embodiment of the present invention is illustrated, a full-vagina sleeve cylindrical expansion and pneumoperitoneum integrated device, comprising:

an elastic embedded ring 1 which is made of elastic material and embedded inside a pelvic outlet, wherein the elastic embedded ring 1 capable of expanding in a natural state inside a vagina to tightly adhere to a wall of the vagina, or being inflated into an annular ring which tightly adheres to the vagina wall so as to elastically expand a vagina tissue, wherein the annular ring is capable of charging and discharging independently;

a sleeve 2 which is made of elastic material or a non-elastic material and is cylinder-shaped; wherein a front end ring of the sleeve 2 is connected with the elastic embedded ring 1, and a rear end ring extends out of the vagina, an operation mask 3 is fixedly provided on the rear end ring, an operation hole 6 and an observation hole 5 which are capable of being sealed are respectively provided on the operation mask 3, the operation mask 3 serves as an end surface sealing plate, in such a manner that an inflatable sealed space is formed inside the vagina and the sleeve 2., wherein the sleeve is a single-layered structure, and a diameter of the sleeve is greater than the vagina; and a fixing supporter 4 which is liftable for supporting the operation mask 3 and regulating height of the operation mask 3, so as to facilitate operation.

Effects of each part of the present invention are as follows.

The elastic embedded ring 1 is annular ring shaped, or annular ring shaped after being inflated, so as to prevent the sleeve from slipping to fully expand channel of the vagina. The elastic embedded ring is provided in a deep portion of the vagina. A lateral wall of the annular ring firmly adheres to a vagina wall to expand vagina tissue, so as to stretch the sleeve towards a direction out of the vagina to generate a pressure between the elastic embedded ring and an opening of a pelvis, in such a manner that the wall of the vagina is firmly adhered on the annular ring, so that an enclosed space is formed between the vagina and the sleeve. A pelvic cavity has a great space for expanding, so the annular ring can full expand in the pelvic cavity, so as to guarantee a spacious enough space in a channel of the vagina for operation. The annular ring is embedded inside the pelvic outlet, so as to ensure that the annular is not capable of slipping from the vagina.

The sleeve is for expanding the vagina. The sleeve comprises an inner part inside the vagina and an outer part outside the vagina. The inner part of the sleeve does not occupy too much space inside the vagina. A diameter of the sleeve is greater than a diameter of the vagina. Due to the loose of the sleeve and the elastic and shrinking effects of the wall of the vagina, the sleeve after gas filling expansion is tightly pressed on the wall of the vagina, so that an external surface of the sleeve is more tightly adhered to the space of the vagina. Furthermore, after the vagina is fully expanded, a more spacious space is formed inside the sleeve, so as to facilitate surgical operation through the vagina. The outer part of the sleeve effectively stretches the operation space which is sealed towards extracorporal space of the patient, without being limited inside the narrow space of the patient. In addition, an external diameter of the sleeve can be further enlarged, so that the operation mask 3 has an adequate position for providing the operation holes 6 and the observation holes 5 and etc, so as to satisfy the operation condition fully. The sleeve can be designed into various models with different length and thickness according to the requirements of operations and conditions of the vagina.

The operation mask is used for entry and exit of the operation instrument. In FIG. 2, the operation instrument is a handling tong 11. Due to extension effect of the sleeve, the operation mask 3 is provided outside the vagina. An area of the operation mask can be enlarged appropriately according to the requirements of the laparoscopic operation. A plurality of operation holes 5 and observation holes 6 with various sizes is provided on the operation mask 3. A valve is fixedly provided in the operation holes 5, or the observation holes 6, or the valve is additionally installed; or otherwise, a puncture outfit comprising the valve, which is utilized in a conventional laparoscope, is provided inside the operation holes 5 or the observation holes 6. Idle holes in the operation are filled and sealed by an air lock. A sealed operation mask made of elastic material can be adopted, so as to assured that the operation mask can be punctured by outfit utilized in the conventional art Retraction effect of the elastic material is depended upon for sealing space and regulating along direction of the surgical operation. After being inflated by a gas tube 9 through the observation holes 5, the operation holes 6 or an inflation hole provided on the operation mask or the sleeve, a pressure is formed in a sealed cavity of the vagina, so as to full expand the vagina in a cylindrical shape and push up uterus 7. When the cavity 8 of the vagina (a front part or a rear part of the cavity) is cut, a pressure can be generated in the vagina and the abdominopelvic cavity which are sealed to form a fully expanded vagina channel and expose surgical field of pneumoperitoneum. Laparoscopic operation instrument with a long handle takes the observation holes as a pivot, so as to maintain the surgical operation in a steady and precise state. A laparoscope 10 supported in the observation hole is for observing operation process mentioned above.

A bottom of the fixing supporter is provided on the ground, an up portion of the fixing frame 4 is for fixing the operation mask or bearing a steady operation mask for a platform. If the operation mask is fixed and controlled by a mechanical arm aside an operation table, the fixing frame 4 is not required.

By utilizing the device of the present invention, an incision is not cut on a dominal wall, so as to avoid leaving scars on the dominal wall. As an auxiliary surgical instrument, the full-vagina sleeve cylindrical expansion and pneumoperitoneum integrated device combines advantages of the conventional gynecologic laparoscopic operations and the conventional vagina operations, enhances advantages and avoids disadvantages of the two kinds of operations, so as to achieve a more minimal invasion in treating gynecopathy.

What is claimed is:

1. A full-vagina sleeve cylindrical expansion and pneumoperitoneum integrated device, comprising:

an elastic embedded ring (1) which is made of elastic material and embeddable inside a pelvic outlet, wherein the elastic embedded ring (1) capable of expanding in a natural state inside a vagina to tightly adhere to a wall of the vagina, or being inflated into an annular ring which tightly adheres to the vagina wall so as to elastically expand a vagina tissue; and a sleeve (2) which is made of elastic material or a non-elastic material and is cylinder-shaped;

wherein a front end ring (12) of the sleeve (2) is connected with the elastic embedded ring (1), and a rear end ring (13) extends out of the vagina, an operation mask (3) is fixedly provided on the rear end ring (13), an operation hole (6) and an observation hole (5) which are capable of being sealed are respectively provided on the operation mask (3), the operation mask (3) serves as an end surface sealing plate, in such a manner that an inflatable sealed space is formable inside the vagina and the sleeve (2).

2. The full-vagina sleeve cylindrical expansion and pneumoperitoneum integrated device, as recited in claim 1, wherein a fixing supporter (4) which is liftable is provided on the full-vagina sleeve cylindrical expansion and pneumoperitoneum integrated device, and the operation mask (3) is supported by the fixing supporter (4).

\* \* \* \* \*